United States Patent [19]

Connor et al.

[11] Patent Number: 5,177,259

[45] Date of Patent: Jan. 5, 1993

[54] DIARYLALKANOIDS HAVING ACTIVITY AS LIPOXYGENASE INHIBITORS

[75] Inventors: David T. Connor, Ann Arbor, Mich.; Daniel L. Flynn, Mindelein, Ill.

[73] Assignee: Warner-Lambert Company, Morris Plains, N.J.

0

[21] Appl. No.: 750,369

[22] Filed: Aug. 27, 1991

Related U.S. Application Data

[60] Division of Ser. No. 541,686, Jun. 21, 1990, which is a division of Ser. No. 266,035, Nov. 2, 1988, Pat. No. 4,959,503, which is a continuation-in-part of Ser. No. 16,897, Mar. 3, 1987, Pat. No. 4,810,716, which is a continuation-in-part of Ser. No. 851,003, Apr. 11, 1986, abandoned.

[51] Int. Cl.$^5$ .................... C07C 59/90; C07C 62/32
[52] U.S. Cl. .................... 562/463; 560/35; 560/53; 562/440; 564/265; 568/325
[58] Field of Search ............ 562/463, 440; 560/53, 560/35; 564/265; 568/325

[56] References Cited

U.S. PATENT DOCUMENTS

| 4,158,063 | 6/1979 | Hitzel et al. |
| 4,562,201 | 12/1985 | Stout et al. |
| 4,695,648 | 9/1987 | Agback et al. ............ 560/53 |
| 4,733,002 | 3/1988 | Yokoyama et al. ............ 568/325 |
| 4,742,083 | 5/1988 | Ritchey et al. |
| 4,761,503 | 8/1988 | Partis et al. ............ 568/313 |
| 4,816,487 | 3/1989 | Schewe et al. |
| 4,937,371 | 6/1990 | Carson et al. ............ 560/53 |
| 5,089,654 | 2/1992 | Yokomori et al. ............ 560/53 |

FOREIGN PATENT DOCUMENTS

| 0006254 | 1/1980 | European Pat. Off. |
| 0163270 | 12/1985 | European Pat. Off. |
| 2381765 | 9/1978 | France. |
| 59-98026 | 6/1984 | Japan. |

OTHER PUBLICATIONS

CA 92:18078lm Page 615 (1980).
Itokawa et al, "Synthesis of Diaryheptanoids and Assessment of Their Pungency", Chemical & Pharmaceutical Bulletin, 31 (7), pp. 2491-2496 (1983).

Primary Examiner—José Dees
Assistant Examiner—B. Frazier
Attorney, Agent, or Firm—Joan Thierstein; Ronald A. Daignault

[57] ABSTRACT

The present invention is novel diarylalkanoids having activity as lipoxygenase inhibitors, novel pharmaceutical compositions therefor, and novel methods of use in treating asthma, allergies, cardiovascular diseases, migraines, psoriasis and immunoinflammatory diseases for diarylalkanoids. The compounds of this invention are also useful as cytoprotective agents.

1 Claim, No Drawings

DIARYLALKANOIDS HAVING ACTIVITY AS LIPOXYGENASE INHIBITORS

CROSS-REFERENCE TO RELATED APPLICATIONS

This is a divisional of U.S. application Ser. No. 541,686 filed Jun. 21, 1990, which is a divisional of U.S. application Ser. No. 266,035 filed Nov. 2, 1988, now U.S. Pat. No. 4,959,503 which is a continuation-in-part of U.S. application Ser. No. 016,897 filed Mar. 3, 1987, now U.S. Pat. No. 4,810,716 which is a continuation-in-part of U.S. application Ser. No. 851,003 filed Apr. 11, 1986, now abandoned.

BACKGROUND OF THE INVENTION

The present invention relates to novel compounds, pharmaceutical compositions and methods of use for the treatment of diseases in which 5-lipoxygenase enzyme activity contributes to the pathological condition. Thus, the novel compounds of the present invention have activity useful for treating asthma, allergies, cardiovascular diseases, migraines, psoriasis, immunoinflammatory conditions, and as cytoprotective agents.

More particularly the novel compounds having the formula I as defined below inhibit 5-lipoxygenase enzymes. Lipoxygenase pathway products such as the leukotrienes B4, C4, D4, and E4, 5-hydroxyeicosatetraenoic acid, 5-hydroperoxyeicosatetraenoic acid, and 12-hydroxyeicosatraenoic acid are related to the above described conditions. Specific conditions for use of the present novel lipoxygenase-inhibiting compounds, pharmaceutical compositions thereof and the novel method of use in accordance with the present invention include allergy; asthma; arthritis; skin disorders including psoriasis and acne; inflammation—including inflammatory bowel diseases or pain; and cardiovascular disorders including myocardial ischemia and infarction, angina, arrhythmias, stroke, migraine and atherosclerosis.

Itokawa, H. et al, "Synthesis of Diarylheptanoids and Assessment of Their Pungency," *Chem. Pharm. Bull.*, 31, 2491 (1983) and "A Pungent Principle from *Alpina Oxyphylla*," *Phytochemistry*, 21, 241 (1982) disclose compounds:

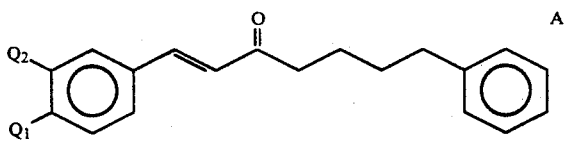

and

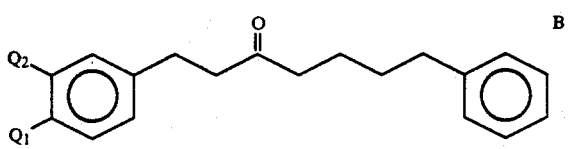

wherein $Q_1$ and $Q_2$ are independently hydrogen, hydroxy or methoxy, correlating structure and pungency with previously published pain-producing experiments on capsaicin congeners.

European Patent Application 163270A also discloses analogs of compound A.

Itokawa, H. et al, "Two New Diarylheptanoids from *Alpinia Offcinarum* Hance," *Chem. Pharm. Bull.*, 29(8) 2383-5 (1981) disclose a compound from those of formula B above as a fraction of an extract which extract was used in Chinese medicine to relieve gastrointestinal disorders as well as fractions of which were known to contract the ileum of guinea pigs. Further, prostaglandin-biosynthesis inhibition having use as an antiinflammatory, antipyretic, analgesic or antiarteriosclerotic is disclosed in J5 9098-026-A (Derivent Abstract No. 84-178335/29) for the compound C as follows:

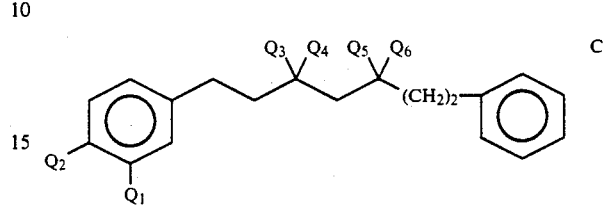

wherein $Q_1$ and $Q_1$ are within the groups defined above therefor and $Q_2$ is hydrogen or together with $Q_4$ is

$Q_5$ and $Q_6$ are hydrogen, optionally form a double between the 5- and 4-position carbon or together are

Finally, European Patent Application 149,242 discloses a compound of formula D:

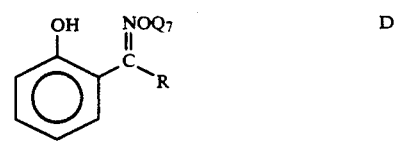

in which $Q_7$ is hydrogen, alkyl, $COQ_9$ or $CONHQ_9$ wherein $Q_9$ is an aliphatic or an aromatic group, R is alkyl or aralkyl, and the phenyl to which

attaches may be substituted at the 2-, and/or 4-position by alkyl or chlorine and at the 3-position by alkyl or OQ′ wherein Q′ is alkyl, cycloalkyl or aralkyl. The compounds of formula D are said to be useful as lipoxygenase inhibitors.

However, the present novel compounds, pharmaceutical compositions and novel methods of using compounds as defined in the present invention are combinations of substituents on various moieties that are not taught or are unobvious from the very limited disclosures of the above references. The compounds of the limited disclosures are excluded herein.

Of lesser interest are diaryl containing compounds linked by carbons having 2 alternating oxygen containing carbons. These compounds are related to curcumin and are disclosed in the European Patent Application 149,242 noted above; by Rao, et al in "Antiinflammatory Activity of Curcumin Analogues," *Indian J. Med. Res.*, 75 574-8 (April 1982), and by Pabon, "A Synthesis of Curcumin and Related Compounds," Recueil, 83 379-386 (1964).

SUMMARY OF THE INVENTION

The present invention is a novel compound of the formula:

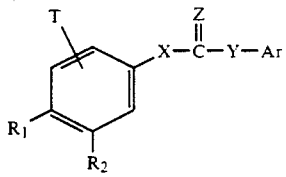

or pharmaceutically acceptable base or acid addition salts thereof, wherein (a) $R_1$ is (i) hydroxy, (ii) lower alkoxy, (iii) $COOR_3$ wherein $R_3$ is hydrogen or lower alkyl, (iv) lower alkanoyl, (v) $NR_3R_4$ wherein $R_3$ and $R_4$ are independently hydrogen or lower alkyl, (vi)

wherein $R_3$ is independently as defined above, (vii)

wherein $R_3$ is independently as defined above, (viii)

wherein $R_3$ is independently as defined above, or (ix)

wherein $R_3$ is independently as defined above:

(b) $R_2$ is (i) hydroxy, (ii) lower alkoxy, (iii) lower thioalkoxy, (iv) lower alkanoyl, (v) halogen, (vi) trifluoromethyl, (vii) hydroxymethyl, (viii) lower alkyl, (ix) $NR_3R_4$ wherein $R_3$ and $R_4$ are independently hydrogen or lower alkyl, (x) nitro, (ix)

wherein $R_3$ is independently as defined above, (xii)

wherein $R_3$ is independently as defined above, (xiii)

wherein $R_3$ is independently as defined above, (xiv)

wherein $R_3$ is independently as defined above, or (xv)

wherein $R_3$ is independently as defined above;

(c) T is (i) hydrogen, ii) lower alkyl, (iii) hydroxy, (iv) lower alkanoyl, (v) $NR_3R_4$ wherein $R_3$ and $R_4$ are independently as defined above, vi) nitro, (vii) halogen, (viii) trifluoromethyl, (ix) lower alkoxy, (x) lower thioalkoxy, (xi)

wherein $R_3$ is independently as defined above, (xii)

wherein $R_3$ is independently as. defined above, or (xiii)

wherein $R_3$ is independently as defined above, (xiv)

wherein $R_3$ is as defined above;

(d) Z is (i) oxygen, (ii) sulfur, (iii) $NOR_3$ wherein $R_3$ is independently as defined above, or (iv) NH;

(e) X and Y are independently (i) $(CH_2)_n$, (ii) $CH=CH$, (iii) $(CH_2)_nM$, wherein n is an integer of one to four and M is oxygen, $NR_3$ wherein $R_3$ is independently as defined above, or $S(O)q$ wherein q is zero, one or two, or (iv) $CH=CH(CO_2R_3)$ wherein $R_3$ is independently as defined above;

(f) Ar is (i) phenyl or naphthyl each of which is unsubstituted or substituted by one, two or three substituents comprising one or more of each of lower alkyl, hydroxy, lower alkoxy, lower thioalkoxy, lower alkanoyl, halogen, trifluoromethyl, lower carboalkoxy, hydroxymethyl, $NR_3R_4$ wherein $R_3$ and $R_4$ are independently as defined above, nitro, COR₃ wherein R₃ is independently as defined above, or

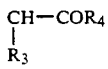

wherein R₃ and R₄ are independently as defined above, or (ii) a heteroaryl unsubstituted or substituted on one or two carbons by one or more of each of lower alkyl, hydroxy, lower alkoxy, lower alkanoyloxy, lower carboalkoxy, halogen, trifluoromethyl, hydroxymethyl, NR₃R₄ wherein R₃ and R₄ are independently as defined above,

wherein R₃ is independently as defined above or

wherein R₃ and R₄ are independently as defined above; in which the heteroaryl comprises pyrrolyl, furanyl, thiophenyl, oxazolyl, thiazolyl, imidazolyl, isothiazolyl, isoxazolyl, or pyrazolyl; and with the overall proviso that when T is hydrogen, R₁ is hydroxy or methoxy, R₂ is hydroxy, lower alkyl, or lower alkoxy, X is (CH₂)ₙ CH=CH, Y is (CH₂)ₙ, and Ar is phenyl or phenyl substituted by lower alkyl then Z cannot be oxygen.

The present invention also relates to a pharmaceutical composition for treating a disease such as allergy, asthma, arthritis, psoriasis, acne, inflammation, pain, ulcerogenic, or cardiovascular disorders comprising an antiallergy, antiasthma, antiarthritis, antipsoriatic, antiacne, antiinflammatory, analgesic, cytoprotective or cardiovascular beneficially effective amount of the compound I as defined above with a pharmaceutically acceptable carrier, and to a method of treating a mammal having one of the diseases noted above by administering to such mammals a dosage form of a compound of the formula I wherein R₁, R₂, T, Z, X, Y and Ar are as defined above but with the proviso limited only to exclude compounds where R₁ is hydroxy or lower alkoxy, R₂ is hydroxy, lower alkyl, or lower alkoxy, or X is (CH₂)ₙ and T is hydrogen, Y is (CH₂)ₙ, and Ar is phenyl or phenyl substituted by lower alkyl when overall Z is oxygen.

Finally, the present invention is a process for preparing compounds of formula I as defined above.

DETAILED DESCRIPTION OF THE EMBODIMENTS

In the compounds of formula I the term "lower alkyl" is meant to include a straight or branched alkyl group having one to four carbon atoms, such as, for example, methyl, ethyl, propyl, or butyl and isomers thereof.

Halogen includes particularly fluorine, chlorine or bromine.

Lower alkoxy and thioalkoxy are O-alkyl or S-alkyl, respectively, of from one to four carbon atoms as defined above for "lower alkyl".

Lower alkanoyl is a

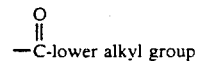

having lower alkyl as defined above.

Appropriate compounds of formula I are useful in the free base form, in the form of base salts where possible, and in the form of acid addition salts. The three forms are within the scope of the invention. In practice, use of salt form amounts to use of the base form. Pharmaceutically acceptable salts within the scope of the invention are those derived from mineral acids such as hydrochloric acid and sulfuric acid; and organic acids such as ethanesulfonic acid, benzenesulfonic acid, p-toluenesulfonic acid, and the like, giving the hydrochloride, sulfamate, ethanesulfonate, benzenesulfonate, p-toluenesulfonate, and the like, respectively or those derived from bases such as suitable organic and inorganic bases. Examples of suitable inorganic bases for the formation of salts of compounds of this invention include the hydroxides, carbonates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di- or trihydroxyalkylamines such as mono-, di-and triethanolamine; amino acids such as arginine, and lysine; guanidine; N-methylglucosamine; N-methylglucamine; L-glutamine; N-methylpiperazine; morpholine; ethylenediamine; N-benzylphenethylamine; tris(hydroxymethyl)aminomethane; and the like. (See for example, "Pharmaceutical Salts," *J. Pharm. Sci.* 66(1):1–19 (1977).)

The acid addition salts of said basic compounds are prepared either by dissolving the free base of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution.

The compounds of the invention may contain an asymmetric carbon atom. Thus, the invention includes the individual stereoisomers, and mixtures thereof. The individual isomers may be prepared or isolated by methods known in the art.

Compounds of the present invention that are preferred are of formula I wherein Z is oxygen or NOR₃ wherein R₃ is hydrogen and Y is (CH₂)₂.

More preferred compounds of the present invention are the preferred compounds of formula I wherein Z is oxygen, R₁ is hydroxy and R₂ is halogen or trifluoromethyl.

Most preferred compounds of the present invention are as follows:

1-Pentene-3-one, 1-(3-amino-4-hydroxyphenyl)-5-phenyl;

1-Hepten-3-one, 1-(4-hydroxy-3-methoxyphenyl)-7-phenyl, oxime;

1-Hepten-3-one, 1-(3,4-dihydroxyphenyl)-7-phenyl, oxime;

1-Penten-3-one, 1-(4-hydroxy-3-methoxyphenyl)-5-phenyl, oxime;

1-Penten-3-one, 1-(3-amino-4-hydroxyphenyl)-5-phenyl, oxime, (both isomer A and isomer B);

1-(4-Hydroxy-3-methoxyphenyl)-4-phenoxy-1-buten-3-one oxime;

1-(4-Hydroxy-3-methoxyphenyl)-6-phenoxy-1-hexen-3-one oxime; and 1-(4-Hydroxy-3-methoxyphenyl)-7-phenyl-1-hepten-3-one, O-methyl oxime.

Preferred methods of treatment are as defined herein using the above noted preferred, more preferred and most preferred compounds of the formula I and the compound 1-(3,4-dihydroxyphenyl)-7-phenyl-1-hepten-3-one which compound is previously disclosed by Itokawa, et al as noted above but having no previously known pharmaceutical utility.

The present invention is also a pharmaceutical composition comprising an effective amount of a compound having the formula I as defined above together with a pharmaceutically acceptable carrier. An effective amount is the amount useful for treating or ameliorating a number of diseases or conditions comprising an inhibition of a lipoxygenase effect. The diseases or conditions are readily recognized for the pathogenesis affected by the inhibitory lipoxygenase effect as recited herein.

Thus, in accordance with the present invention, another aspect of the invention, provides a method of administering to mammals, including humans, in need of treatment or amelioration of diseases or conditions an amount effective for treatment of the diseases or conditions of a compound or composition having the formula I as defined above. The need is evident for diseases or conditions benefiting from inhibition of a lipoxygenase effect.

By virtue of the activity of the compounds having the formula I of the present invention as inhibitors of 5-lipoxygenase such compounds are useful in treating asthmas and allergies as well as cardiovascular disorders, migraine, and immuno-inflammatory conditions as recited above.

The antiasthma and antiallergic activity provides methods of treatment for hypersensitivity reaction having broad symptoms. For example, the symptoms may include dermatitis, lacrimation, nasal discharge, coughing, sneezing, nausea, vomiting, diarrhea, difficulty in breathing, pain, inflammation, and in severe cases, anaphylactic shock and circulatory collapse. The symptoms may be found in man as well as other animals suffering from bronchial asthma, seasonal pollinosis (e.g., hay fever), allergic rhinitis, urticaria, allergic conjunctivitis, food allergies, and anaphylactoid reactions.

Likewise, the activity of the compounds of formula I provides a method of treatment for cardiovascular disorders, particularly ischemia and myocardial infarctions. The symptoms of a subject having a cardiovascular disorder may be determined by special diagnostic procedures directed to subjects having a history, general physical appearance and then detailed deviations from normal appearances suggesting a cardiovascular disorder. Such disorders are also found in man as well as other mammals. Symptoms of the disorders are described extensively in *The Merck Manual* 14th ed., (1982).

Further, method of treatment is provided by the compounds of formula I herein for migraine, stroke and inflammation. The symptoms requiring treatment for these purposes are also readily recognized, particularly for migraine in man and/or inflammation in man as well as other mammals.

The compounds of this invention are also useful as cytoprotective agents.

Pharmaceutical compositions which also are the present invention are prepared from the compound of formula I and salts thereof described as the present invention having inert pharmaceutical carriers. The compositions may be either solid or liquid.

A physician or veterinarian of ordinary skill readily determines a subject who is exhibiting symptoms described herein. Regardless of the route of administration selected, the compounds of the present invention are formulated into pharmaceutically acceptable dosage forms by conventional methods known to the pharmaceutical art.

The compounds can be administered in such oral unit dosage forms such as tablets, capsules, pills, powders, or granules. They also may be administered rectally or vaginally in such forms as suppositories or bougies; they may also be introduced parenterally (e.g., subcutaneously, intravenously, or intramuscularly), using forms known to the pharmaceutical art. They are also introduced directly to an affected area (e.g., in the form of eye drops or by inhalation). For the treatment of asthma or allergies such as erythema, and dermatological disorders such as psoriasis and acne, the compounds of the present invention may also be administered topically in the form of ointments, creams, gels, or the like. However, in general, the preferred route of administration is orally.

An effective but nontoxic quantity of the compound is employed in treatment. The ordinarily skilled physician or veterinarian will readily determine and prescribe the effective amount of the compound to prevent or arrest the progress of the condition for which treatment is administered. In so proceeding, the physician or veterinarian could employ relatively low dosages at first, subsequently increasing the dose until a maximum response is obtained.

Initial dosages of the compounds of the invention having formula I are ordinarily in the area of 10 mg up to 2 g per day orally, preferably 10 mg to 500 mg per dose orally, given from one to four times daily or as needed. When other forms of administration are employed equivalent doses are administered.

The compounds of the invention are capable of forming both pharmaceutically acceptable acid addition and/or base salts. Base salts are formed with metals or amines, such as ammonium, alkali, and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylflucamine, and procaine.

Pharmaceutically acceptable acid addition salts are formed with organic and inorganic acids.

Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, arginine, and the like. The salts are prepared by contacting the free base form with a sufficient amount of the desired acid to produce either a mono or di, etc. salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The compounds of the invention can exist in unsolvated as well as solvated forms, including hydrated forms. In general, the solvated forms, including hydrated forms and the like are equivalent to the unsolvated forms for purposes of the invention.

Finally, the methods of preparation for compounds of formula I' are as generally as follows:

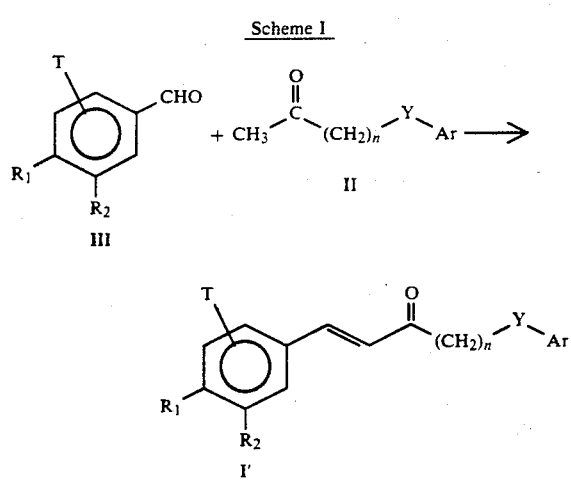

wherein T, $R_1$, $R_2$ (except when $R_2$ is $NR_3R_4$), n, Y and Ar are as defined above.

A methyl ketone of formula II in a solvent, such as diethyl ether, or the like is added to a mixture of pyrrolidine and acetic acid. Then, a solution of an analog of benzaldehyde having the formula III wherein T and $R_1$ are as defined above and $R_2$ is as defined above (except when $R_2$ is amino), in a solvent such as diethyl ether, tetrahydrofuran (THF), dimethoxyethane (DME) or the like is added dropwise and stirred at about room temperature for about 12 to 48 hours to provide a condensation product of formula I' wherein T, $R_1$, n, Y and Ar are as defined above and $R_2$ is as defined above except when $R_2$ is amino.

When $R_2$ is amino as shown in a compound of formula IV a compound of formula I" is reduced by conventional methods using Raney Nickel to obtain the compound of formula IV wherein T, R, n, Y and Ar are as defined above and $R_2$ is amino. The following Scheme II illustrates this reduction.

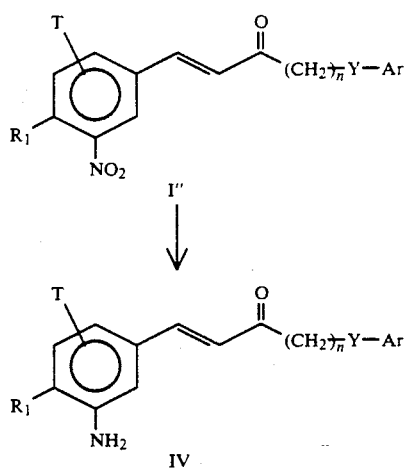

wherein T, $R_1$, n, Y and Ar are as defined above.

Alternatively, Scheme III illustrates a specific preparation for a compound of formula VI comprising a compound of formula III as defined above and a phosphorane of the formula V wherein Y and Ar are as defined above are dissolved in a solvent such as toluene, THF, dimethylsulfoxide (DMSO) or the like and warmed to reflux for from two to five hours, preferably three hours. The resulting product is treated in tetrahydrofuran, ethylacetate (EtOAc), or the like with an excess of sodium bisulfite dissolved in water. The treatment is at 0° to 25° C. preferably 25° C. for about one to three hours, preferably about one hour. The phosphorane of formula V is prepared in a manner analogous to that described by Le Carre: *C. R. Acad. Sci. Paris,* 273, 81 (1971). This alternative process is shown in Scheme III as follows:

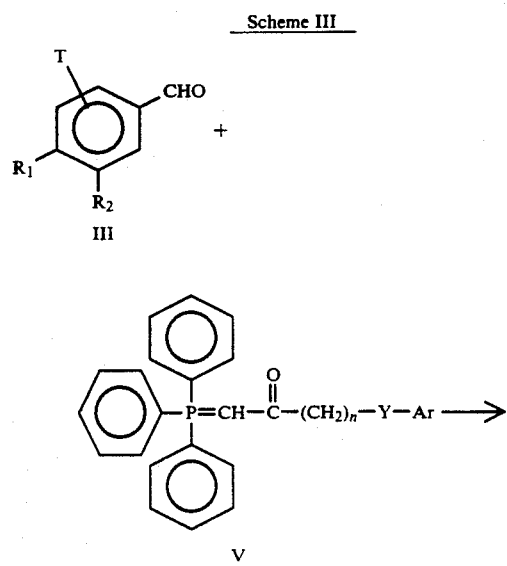

-continued
Scheme III

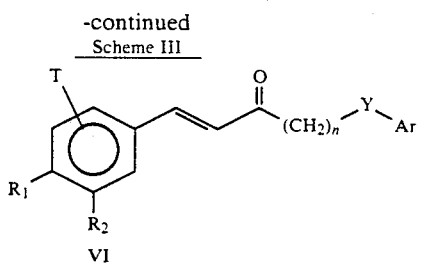

wherein T, $R_1$, n, Y and Ar are as defined above and $R_2$ is as defined above except $R_2$ is not the amino group.

Finally, the compounds of formula VII are prepared as shown in the following Scheme IV in which a compound of formula I', IV or VI having the definitions noted above are dissolved in a solvent such as methanol, ethanol, iso-propanol or the like. Hydroxyamine and sodium acetate are added to the solution and the resulting solution stirred for two hours at about room temperature giving the compound of formula VII.

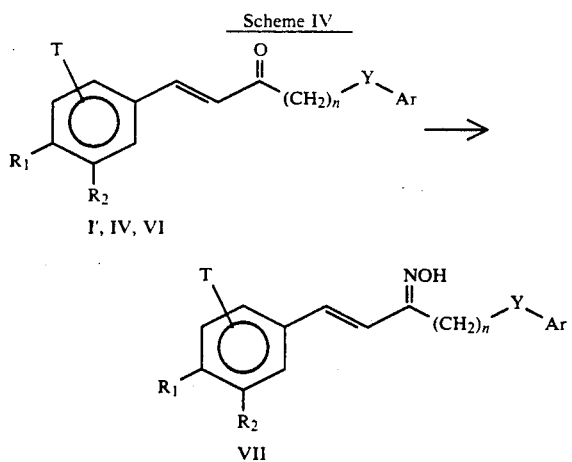

wherein T, $R_1$, $R_2$, n, Y and Ar are as defined above.

Compounds of formula I wherein Z is sulfur can be prepared by using methods analogous to those known in the art. Likewise, compounds wherein X is $(CH_2)_n$ can be prepared using appropriate alkenylene containing compounds of formula I which are then hydrogenated by conventional methods. One of skill in the art would recognize variations in the sequence which may be appropriately used in the processes to make the compounds of formula I herein.

Under certain circumstances it is necessary to protect either the N or O of intermediates in the above noted process with suitable protecting groups which are known. Introduction and removal of such suitable oxygen and nitrogen protecting groups are well-known in the art of organic chemistry; see for example "Protective Groups in Organic Chemistry," J. F. W. McOmie, ed., (New York, 1973), pages 43ff, 95ff, J. F. W. McOmie, Advances in Organic Chemistry, Vol. 3, 191-281 (1963); R. A. Borssonas, Advances in Organic Chemistry, Vol. 3, 159-190 (1963); and J. F. W. McOmie, Chem. & Ind., 603 (1979).

Examples of suitable oxygen protecting groups are benzyl, t-butyldimethylsilyl, ethoxyethyl, and the like.

Protection of an N-H containing moiety is necessary for some of the processes described herein for the preparation of compounds of this invention. Suitable nitrogen protecting groups are benzyl, triphenylmethyl, trialkylsilyl, trichloroethylcarbamate, trichloroethoxycarbonyl, vinyloxycarbamate, and the like.

Under certain circumstances it is necessary to protect two different oxygens with dissimilar protecting groups such that one can be selectively removed while leaving the other in place. The benzyl and t-butyldimethylsilyl groups are used in this way; either is removable in the presence of the other, benzyl being removed by catalytic hydrogenolysis, and t-butyldimethylsilyl being removed by reaction with, for example, tetra-n-butylammonium fluoride.

In the process described herein for the preparation of compounds of this invention the requirements for protective groups are generally well recognized by one skilled in the art of organic chemistry, and accordingly the use of appropriate protecting groups is necessarily implied by the processes of the charts herein, although not expressly illustrated.

The products of the reactions described herein are isolated by conventional means such as extraction, distillation, chromatography, and the like.

The salts of compounds of formula I described above are prepared by reacting the appropriate base or acid with a stoichiometric equivalent of the compounds of formula I, respectively, to obtain pharmaceutically acceptable salts thereof.

DESCRIPTION OF THE PREFERRED EMBODIMENTS

The invention is further elaborated by the representative examples as follows. Such examples are not meant to be limiting.

EXAMPLE 1

1-(3-Hydroxy-4-methoxyphenyl)-7-phenyl-1-hepten-3-one

Pyrrolidine (2.42 g, 34.0 mMol) is added to acetic acid (2.04 g, 34.0 mMol), and the mixture is stirred at room temperature for 20 minutes. After this time, 6-phenyl-2-hexanone (4.00 g, 22.6 mMol) as a solution in diethyl ether (20 ml) is added, and the mixture is allowed to stir for an additional 15 minutes. An ethereal solution of iso-vanillin (3.45 g, 22.5 mMol) is then added dropwise. The reaction mixture is stirred for 48 hours. HCl (1.0N, 30 ml) is then added to the reaction mixture, and the contents stirred for 20 minutes. The mixture is then taken up into an equal volume of ethyl acetate, and the phases separated. The organic layer is washed with saturated aqueous sodium bicarbonate, dried (sodium sulfate), and concentrated. The residue is chromatographed (silica gel; hexane/ethyl acetate 3:1) to afford 1.0 g (28%) of 1-(3-hydroxy-4-methoxyphenyl)-7-phenyl-1-hepten-3-one, mp=70°-75° C. C, H analysis: Calcd. for $C_{20}H_{22}O_3$ (77.39, 7.14); Found (77.68, 6.94). The procedure of Example 1 is within that described in the above cited reference by Itokawa H. et al in the Chem. Pharm. Bull. Similarly prepared are Examples 2-12 using the procedure of Example 1.

TABLE 1

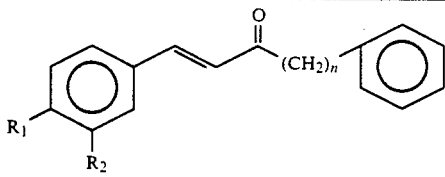

| Example | $R_1$, $R_2$ | n | Yield (%) | mp (°C.) | Elemental Analysis C, H, N (Calcd) C, H, N (Found) |
|---|---|---|---|---|---|
| 2* | 3,4-(OH)$_2$ | 4 | 20 | 110–115 | 77.00, 6.80 |
|  |  |  |  |  | 77.20, 6.71 |
| 3* | 4-OH | 4 | 28 | 82–85 | 80.81, 7.85 |
|  |  |  |  |  | 81.20, 7.78 |
| 4 | 3-CH$_3$OH, 4-OH | 4 | 30 | 65–68 | 77.98, 6.04 |
|  |  |  |  |  | 78.27, 6.16 |
| 5 | 3-Cl, 4-OH | 4 | 45 | 72–74 | 72.49, 6.08 |
|  |  |  |  |  | 72.42, 6.21 |
| 6 | 4-COOH | 4 |  | 160–162 | 71.20, 5.27 |
|  |  |  |  |  | 71.40, 5.32 |
| 7* | 3-OMe, 4-OH | 3 | 29 | (Oil) | 75.85, 6.87 |
|  |  |  |  |  | 75.79, 7.00 |
| 8* | 3,4-(OH)$_2$ | 3 | 51 | 141–145 | 76.57, 6.42 |
|  |  |  |  |  | 75.84, 6.75 |
| 9* | 3-OMe, 4-OH | 2 | 50 | 70–76 | 71.55, 6.73 |
|  |  |  |  |  | 71.38, 6.45 |
| 10 | 3-CH$_2$OH, 4-OH | 2 | 54 | 122–128 | 76.57, 6.42 |
|  |  |  |  |  | 76.38, 6.51 |
| 11 | 3-Cl, 4-OH | 2 | 40 | 128–132 | 71.20, 5.27 |
|  |  |  |  |  | 71.40, 5.32 |
| 12 | 3-NO$_2$, 4-OH | 2 | 56 | 115–118 | 68.68, 5.08, 4.71 |
|  |  |  |  |  | 68.37, 5.22, 4.67 |

*See Itokawa, H. et al. "Synthesis of Diarylheptanoids and Assessment of Their Pungency," Chem. Pharm. Bull., 31, 2491 (1983).

EXAMPLE 13

1-Penten-3-one, 1,5-bis(4-hydroxy-3-methoxyphenyl)-

1,5-bis(4-hydroxy-3-methoxyphenyl)-1-penten-3-one is prepared according to the procedure of Example 1 from vanillin and 3-methoxy-4-hydroxybenzylacetone in 45% yield. C, H analysis: Calcd for C$_{19}$H$_{20}$O$_5$ (69.50, 6.13); Found (69.52, 6.15).

EXAMPLE 14

1-(4-Hydroxy-3-methoxyphenyl)-6-phenoxy-1-hexene-3-one

According to the procedure of Example 1, 1-(4-hydroxy-3-methoxyphenyl)-6-phenoxy-1-hexene-3-one is prepared from vanillin and 5-phenoxy-2-pentanone in 40% yield, mp=67°–70° C. C, H analysis: Calcd for C$_{19}$H$_{20}$O$_4$·0.1H$_2$O (72.67, 6.50); Found (72.48, 6.49).

EXAMPLE 14A

Following to the procedure of Example 1, and using appropriate starting materials in THF or THF and DMF mixture as solvent, the following compounds are prepared and purified by extensive chromatography to separate it from other isomeric products.

| Example | $R_1$, $R_2$ | Yield (%) | mp | Anal | % C | % H | % Br |
|---|---|---|---|---|---|---|---|
| 14A | 3-MeO, 5-Br | 20.8 | 114–118 | C, H, Br | 59.85, | 4.74, | 22.12 |
|  |  |  |  |  | 59.67, | 4.75, | 22.08 |
| 14A | 3,5-(MeO)$_2$ | 18.5 | 93–94 | C, H | 73.06, | 6.45 | — |
|  |  |  |  |  | 72.89, | 6.48 | — |
| 14A | 3,5-Me$_2$ | 12.0 | 104–105 | C, H | 81.39, | 7.19 | — |
|  |  |  |  |  | 81.85; | 7.26; | — |
|  |  |  |  |  | 81.73 | 7.36 |  |

EXAMPLE 15

[1-Pentene-3-one, 1-(3-amino-4-hydroxyphenyl)-5-phenyl]

1-Pentene-3-one, 1-(4-hydroxy-3-nitrophenyl)-5-phenyl (3.0 g, 1.0×10$^{-2}$ moles) is reduced to the product in THF (100 ml) in the presence of Raney Nickel (0.2 g) under a pressure of 15 psi. The crude reaction mixture is evaporated to dryness and chromatographed on a flash column using hexane:ethyl acetate 3:1 to give 2.6 g of 1-pentene-3-one, 1-(3-amino-4-hydroxyphenyl)-5-phenyl (99% yield), mp=154°–158° C. C, H, N analysis calculated with 0.2 m H$_2$O C, H, N (75.36, 6.47, 5.19); C, H, N Found (75.36, 6.56, 5.19).

EXAMPLE 16

1-(4'-Hydroxy-3'-methoxyphenyl)-4-phenoxy-1-butene-3-one

4-Hydroxy-3-methoxybenzaldehyde (2.1 g, 13.8 mMol) and 3-phenoxypropane-2-one triphenylphosphorane (2.8 g, 6.9 mMol) (prepared as described by Le-Corre: *C. R. Acad. Sci. Paris,* 273 81 (1971)) are dissolved in 100 ml of toluene and warmed to reflux. After three hours, the solvent is evaporated and the residue is taken up in tHF. Sodium bisulfite (10.0 g) is dissolved in 100 ml of water and stirred with the solution for one hour. The THF is evaporated and the water is extracted with chloroform. Drying over magnesium sulfate and evaporation of the chloroform gives a yellow oil. Flash chromatography in ethyl acetate on silica gel gives 1.5 g (65%) of 1-(4'-hydroxy,3'-methoxyphenyl)-4-phenoxy-1-butene-3-one; mp=85°-87° C. C, H analysis: Calcd for $C_{17}H_{16}O_4$ (71.81, 5.68); Found (71.85, 5.50).

EXAMPLE 16A

2-Oxo-3-(phenylthio)propylidene triphenylphosphorane

Prepared by the method of Banerjee (Prostaglandins, 22, 167-182 (1981)). Yield=50%; mp=133°-135° C.

1-(4-Hydroxy-3-methoxyphenyl)-4-phenylthio-1-butene-3-one

Prepared by the method of Example 16. Flash chromatography in methylene chloride gives 1.3 g (62%) of 1-(4-hydroxy-3-methoxyphenyl)-4-phenylthio-1-butene-3-one; mp=78°-80° C. Analysis for $C_{17}H_{16}O_3S$ requires C-67.97, H-5.38. Found: C-67.88, H-5.31.

EXAMPLE 17

1-Hepten-3-one, 1-(4-hydroxy-3-methoxyphenyl)-7-phenyl, oxime

1-Hepten-3-one, 1-(4-hydroxy-3-methoxyphenyl)-7-phenyl (Ref. H. Itokawa, *Chem. Pharm. Bull.,* 31, 2491 (1983) and as prepared in Example 1 above) (1.50 g, 4.80 mMol) is dissolved in methanol (130 ml) and stirred with hydroxylamine.HCl (2.0 g, 29.0 mMol) and sodium acetate (2.40 g, 29.0 mMol) for two hours at room temperature. The mixture is then evaporated to dryness, redissolved in ethyl acetate (100 ml), and washed with water. The organic layer is then dried (sodium sulfate) and concentrated. Chromatography (silica gel, hexane:ethyl acetate, 3:1) affords a quantitative yield of 1-hepten-3-one, 1-(4-hydroxy-3-methoxyphenyl)-7-phe-nyl-, oxime; mp=115°-118° C. C, H, N analysis: Calcd for $C_{20}H_{33}NO_3$ (73.82, 7.12, 4.30); Found (74.04, 7.12, 4.39).

Following the procedure of Example 17, and using the appropriate starting materials as prepared above or as prepared by analogous methods, the following oximes of Table 2 are prepared.

TABLE 2

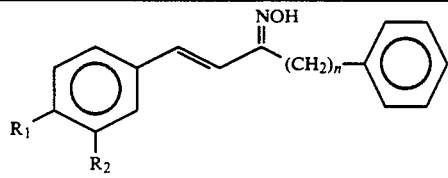

| Example | $R_1, R_2$ | n | Yield (%) | mp (°C.) | Elemental Analysis C, H, N (Calcd) C, H, N (Found) |
|---|---|---|---|---|---|
| 18 | 3-OH, 4-OMe | 4 | 100 | 95–105 | 73.82, 7.12, 4.30 |
|   |   |   |   |   | 74.06, 7.26, 4.03 |
| 19 | 3,4-(OH)$_2$ | 4 | 100 | 137–140 | 73.29, 6.80, 4.50 |
|   |   |   |   |   | 73.19, 6.87, 4.60 |
| 20 | 3-CH$_2$OH, 4-OH | 4 | 100 | 135–138 | 73.82, 7.12, 4.30 |
|   |   |   |   |   | 73.51, 7.53, 4.23 |
| 21 | 3-OMe, 4-OH | 2 | 100 | (Oil) | 71.79, 6.50, 4.65 |
|   |   |   |   |   | 71.79, 6.63, 4.73 |
| 22 | 3-CH$_2$OH | 2 | 100 | 155–158 | 72.71, 6.44, 4.71 |
|   |   |   |   |   | 72.39, 6.58, 4.77 |
| 23 | 3-NH$_2$, 4-OH | 2 | 100 | 143–147 | 73.32, 6.42, 9.92 |
|   |   |   |   |   | 72.91, 6.54, 9.64 |

EXAMPLE 24

1-(4-Hydroxy-3-methoxyphenyl)-4-phenoxy-1-buten-3-one oxime

Following the procedure of Example 17, 1-(4-hydroxy-3-methoxyphenyl)-4-phenoxy-1-buten-3-one oxime is prepared in 39% yield; mp=155°-158° C. C, H, N analysis: Calcd for $C_{17}H_{17}NO_4$ (68.20, 5.74, 4.68); Found (68.26, 6.02, 4.92).

EXAMPLE 24A 1-(4-Hydroxy-3-methoxyphenyl)-4-phenylthio-1-buten-3-one oxime

Following the procedure of Example 17, 1-(4-hydroxy-3-methoxyphenyl)-4-phenylthio-1-butene-3-one oxime is prepared in 28% yield; mp=90°-100° C. C, H, N analysis: Calcd for $C_{17}H_{17}NO_3S$ (64.73, 5.44, 4.44); Found (64.44, 5.48, 4 37).

EXAMPLE 25

1-(4-Hydroxy-3-methoxyphenyl)-6-phenoxy-1-hexen-3-one oxime

Following the procedure of Example 17, 1-(4-hydroxy-3-methoxyphenyl)-6-phenoxy-1-hexen-3-one is prepared in 76% yield. C, H, N analysis: Calcd for $C_{19}H_{21}NO_4 \cdot H_2O$ (66.06, 6.72, 4.06); Found (66.28, 6.80, 4.39).

EXAMPLE 26

1-(4-Hydroxy-3-methoxyphenyl)-7-phenyl-1-hepten-3-one, O-methyl oxime

A mixture of 1-(4-hydroxy-3-methoxyphenyl)-7-phe-nyl-1-hepten-3-one (0.50 g, 1.61 mMol), methoxylamine.HCl (0.403 g, 4.83 mMol), and sodium acetate (0.396 g, 4.83 mMol) is stirred in methanol (10 ml) at room temperature for 12 hours. The mixture is then concentrated and taken up into chloroform. The organic layer is washed with water and brine, and then dried (sodium sulfate). Concentration gives pure 1-(4-hydroxy-3-methoxyphenyl)-7-phenyl-1-hepten-3-one, O-methyl oxime (490 mg) as a semi-solid.

EXAMPLE 27

1-(3-Methoxy-4-hydroxyphenyl)-5-(2-furyl)-1-penten-3-one

Using the method of Example 1 using 1-(2-furyl)-3-butanone bp 75°-78° C. at 10 mm Hg (prepared by the method analogous to Yamashita, *Tet. Let.*, 1975, p. 1867 with a yield of 47%) the 1-(3-methoxy-4-hydroxyphenyl)-5-(2-furyl)-1-pentene-3-one is prepared in 49% yield. mp=82°-84° C. C, H, N analysis: Calcd for $C_{16}H_{16}O_4$ (70.56, 5.93); Found (70.50, 6.14).

EXAMPLE 28

1-(3-Methoxy-4-hydroxyphenyl)-5-(2-furyl)-1-penten-3-one oxime

Using the procedure of Example 17, 1-(3-methoxy-4-hydroxyphenyl)-5-(2-furyl)-1-pentene-3-one oxime is prepared in 61% yield; mp=110°-120° C. C, H, N analysis: Calcd for $C_{16}H_{17}NO_4$ (66.88, 5.98, 4.88); Found 66.57, 6.03, 4.80).

EXAMPLE 28A (E,E)-1-(4-Hydroxy-3,5-dimethoxyphenyl)-5-phenyl-1-penten-3-one oxime (Isomer A) and
(Z,E)-1-(4-hydroxy-3,5-dimethoxyphenyl)-5-phenyl-1-penten-3-one oxime Isomer B)

A mixture of (E)-1-(4-hydroxy-3,5-dimethoxyphenoxyphenyl)-5-phenyl-1-penten-3-one (2.5 g; 8.0 mmol), hydroxylamine hydrochloride (1.84 g; 26.0 mmol) and anhydrous sodium acetate (2.17 g; 26.0 mmol) in MeOH (100 ml is stirred at 24° C. for 18 h. The reaction mixture is evaporated to dryness and the residue decomposed with water and extracted with $CH_2Cl_2$. The $CH_2Cl_2$ extract is evaporated to dryness to give an oil (3.0 g) which is flash chromatographed over silica gel (90 g; 230-400 mesh) using $CHCl_3$ and increasing amount of ethyl acetate as eluents. Elution with 5% ethyl acetate-$CHCl_3$ gives the faster moving product, isomer A, as a single isomer. It is recrystallized from isopropyl ether to give white crystalline solid. Yield 110 mg (4.2%), mp 144°-146° C. TLC (SiO$_2$, CHCl$_3$-AcOEt (3:1)) gives an Rf value of 0.42. It is assigned the stereochemistry of E,E—.

Further elution with 5% AcOEt—CHC$_3$ gives fractions which contain mixtures of isomer A and isomer B as crude solid which is recrystallized from isopropyl ether as white solid. Yield 1.13 g (43%), mp 110°-117° C. TLC (SiO$_2$, CHC$_3$-AcOEt (3:1) gives two spots for isomer A and isomer B with Rf values of 0.42 and 0.33, respectively.

Elution with 10% AcOEt—CHC$_3$ gives isomer B as single product which is recrystallized from isopropyl ether. Yield 0.64 g (24.4%), mp 120°-124° C. TLC (SiO$_2$, CHC$_3$—AcOEt (3:1)) shows it as one spot with Rf value of 0.33. It is assigned the stereochemistry E,Z—.

EXAMPLE 28B

Following the procedure of Example 28A above, the following compounds are synthesized as a mixture of E,E- and E,Z- isomers.

(E,E-)-1(4-Hydroxy-3,5-dimethylphenyl)-5-phenyl-1-penten-3-one oxime and
(Z,E)-1-(r-hydroxy-3,5-dimethylphenyl)-5-phenyl-1-penten-3-one oxime mixture Yield 0.76 g (51.5%), mp 110°-124° C. TLC shows two close spots (SiO$_2$, CHC$_3$,—AcOEt, (3:1)) with Rf values of 0.557 and 0.489 consistent with the structure of the title compound.

EXAMPLE 28C

Following the procedure of Example 14A, the thienyl and furanyl pentenones (where R=O) are prepared. The corresponding oximes are prepared following the procedure of Example 28A or Example 28B. The following examples are prepared as shown in Table 1 as follows.

TABLE 3

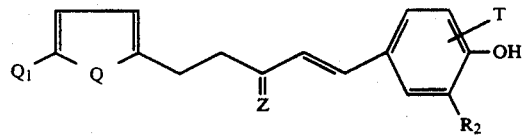

| Example No. | Q | Z | T | R$_2$ | Q$_1$ | MP °C. | Yield Purified % (g) | Purification Solvent | Empirical Formula | C | H | N | Br | S |
|---|---|---|---|---|---|---|---|---|---|---|---|---|---|---|
| | | | | | | | | | | Calcd/Found | | | | |
| 28C1 | O | O | OCH$_3$ | OCH$_3$ | H | 107-109 | 9 (1.4) | Methylene chloride-isopropyl ether | C$_{17}$H$_{18}$O$_5$ | 67.54, 67.25, | 6.0 6.14 | | | |
| 28C2 | O | O | OCH$_3$ | Br | H | 106-107 | 14 (1.51) | Methanol | C$_{16}$H$_{15}$BrO$_4$ | 54.72, 54.64, | 4.31, 4.31, | | 22.75 22.99 | |
| 28C3 | O | NOH | OCH$_3$ | OCH$_3$ | H | 650 | 72 (1.5) | | C$_{17}$H$_{19}$NO$_5$ | 64.34, 63.96, | 6.04, 6.15, | 4.41 4.22 | | |
| 28C4 | S | O | OCH$_3$ | H | H | 75-77 | 38.5 (7.2) | Ethyl acetate-hexane | C$_{16}$H$_{16}$O$_3$S | 66.64, 66.83, | 5.59, 5.53, | | | 11.12 11.15 |
| 28C5 | S | O | OCH$_3$ | OCH$_3$ | H | 117-119 | 46 (7.4) | Ethyl acetate | C$_{17}$H$_{18}$O$_4$S | 64.13, 64.02, | 5.70, 5.67, | | | 10.07 9.69 |
| 28C6 | S | NOH | OCH$_3$ | H | H | 104-110 | 57.4 (2.9) | Ethyl acetate-hexane | C$_{16}$H$_{17}$NO$_3$S | 63.34, 63.12, | 5.65, 5.48, | 4.62 4.53 | | |
| 28C7 | S | NOH | OCH$_3$ | OCH$_3$ | H | 67-70 | 51 (2.7) | Ethyl acetate-hexane | C$_{17}$H$_{19}$NO$_4$S | 61.24, 61.20, | 5.74, 5.64, | 4.20, 4.06, | | 9.62 9.77 |

TABLE 3-continued

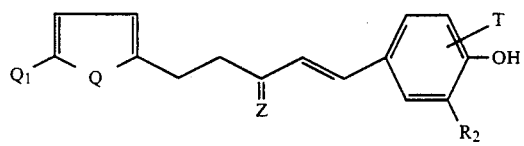

| Example No. | Q | Z | T | R₂ | Q₁ | MP °C. | Yield Purified % (g) | Purification Solvent | Empirical Formula | Analysis C Calcd/Found | H | N | Br | S |
|---|---|---|---|---|---|---|---|---|---|---|---|---|---|---|
| 28C8 | S | O | CH₃ | CH₃ | H | 118–120 | 39 (4.6) | Ethyl acetate-hexane | C₁₇H₁₈O₂S | 71.30, 71.32, | 6.33 6.34 | | | |
| 28C9 | O | O | CH₃ | H | 142–144 | 39.2 (10.59) | Toluene | C₁₇H₁₈O₃ | 75.53, 75.62, 6.71 | 6.66 | | | | |
| 28C10 | S | NOH | CH₃ | CH₃ | H | 123–130 | 65 (2.3) | Ethyl acetate-hexane | C₁₇H₁₉NO₂S | 67.74, 67.95, | 6.35, 6.30, | 4.65, 4.81, | | 10.64 10.98 |
| 28C11 | O | NOH | CH₃ | CH₃ | H | 112–114 | 58.2 (3.8) | Ethyl acetate-hexane | C₁₇H₁₉NO₃ | 71.56, 71.47, | 6.71, 6.86, | 4.91 5.03 | | |
| 28C12 | O | O | ⊥ | H | H | 117–119 | 33.7 (4.41) | Ethyl acetate-hexane | C₁₉H₂₂O₃ | 76.48, 7.43 76.32, 7.40 | | | | |
| 28C13 | O | NOH | ⊥ | H | H | 65–87 | 17.3 (0.6) | Ethyl ether-hexane | C₁₉H₂₃NO₃ | 72.82, 7.40, 4.47 72.63, 7.41, 4.52 | | | | |
| 28C14 | O | O | OCH₃ | ⊥ | H | 115–117 | 34.1 (2.15) | Ethyl ether-hexane | C₂₀H₂₄O₄ | 73.14, 7.37 73.11, 7.60 | | | | |
| 28C15 | O | O | OCH₃ | Br | CO₂CH₃ | 122–123 | 40 (24.6) | Methanol | C₁₈H₁₇BrO₆ | 52.76, | 3.92, | | 19.49 | |
| 28C16 | O | O | ⊥ | H | CO₂CH₃ | 183–185 | 42.8 (6.8) | Methanol | C₂₁H₂₄O₅ | 70.76, 6.79 70.54, 6.67 | | | | |

The starting benzaldehydes are prepared according to the following literature references.

3-tert-Butyl-5-hydroxybenzaldehyde and 3-Bromo-5-tert-butyl-4-hydroxybenzaldehyde, Ikuo Katsume et al. *Chem. Pharm. Bull.*, 1986, 34(1), 121–129.

3-tert-Butyl-5-methoxy-4-hydroxybenzaldehyde, H. Hemetsberger and D. Knittel. *Monatsheften fur chemie*, 1971. 102, 1110–1119.

3-tert-Butyl-5-methyl-4-hydroxybenzaldehyde, S. L. Shapiro et al. *J. Org. Chem.*, 1961, 26, 3580.

EXAMPLE 28D (E)-5-[5-[4-Hydroxy-3-methoxyphenyl)-3-oxo-4-pentenyl]-2-furancarboxylic acid, methyl ester According to the procedure of Example 14A, (E)-5-[5-(4-hydroxy-3-methoxy-phenyl)-3-oxo-4-pentenyl]-2-F-urancarboxylic acid, methyl ester is prepared from methyl-4-(2-furanyl)-2-butan-one-5-carboxylate (S. M. Singh, *Indian J. Chem.* Sect. B, 1979, 18B(4), 363-5) and vanillin. Recrystallization from ethyl acetate-hexane gives 14.6 g (29.5%) of analytically pure product, mp 93°–94° C. C, H analysis: Calculated for C₁₈H₁₈O₆ (65.44, 5.49); Found (65.31, 5.52).

EXAMPLE 28E

5-[5-i4-hydroxy-3-methoxyphenyl)-3-(hydroxyimino)-4-pentenyl]-2-furancarboxylic acid, methyl ester is prepared by the method of Example 17.

Purification by flash chromatography (silica gel, ethyl acetate 95:5 as eluent), afforded a white solid, which after recrystallization from ether-hexane gives 6.4 g (72%) of analytically pure product, mp 110°–125° C. C, H, N analysis: Calculated for C₁₈H₁₉NO₆ (62.60, 5.55, 4.06); Found 62.76, 5.54, 3.90).

EXAMPLE 28F (E)-5[3-(Hydroxyimino)-5-(4-hydroxy-3-methoxyphenyl)-4-pentenyl)-2-furancarboxylic acid A mixture of 5-[5-(4-hydroxy-3-methoxyphenyl)-3-hydroxyimino)-4-pentenyl]-2-furancarboxylic acid, methyl ester (4.4 g, 0.0127 mole), potassium hydroxide (4.2 g) and methanol (200 ml) is refluxed for four hours. Most of the methanol is removed under reduced pressure, <35° C. The residue is dissolved in water. After cooling, the basic solution is carefully acidified with dilute hydrochloric acid and extracted with ether. Drying over sodium sulfate and evaporation of the ether gives 3.9 g of a solid, mp 103°–110° C. Recrystallization from ethyl acetate-hexane gives 0.5 g (11.9%) of (E)-5-[3-(hydroxyimino)-5-(4-hydroxy-3-methoxyphenyl)-4-pentenyl]-2-furancarboxylic acid, mp 187°–189° C. (dec.). C, H, N analysis: Calculated for C₁₇H₁₇NO₆ (61.33, 5.17, 4.23); Found (61.35, 5.11, 4.04).

EXAMPLE 28G (E,E)-1-(3-Bromo-4-hydroxy-5-methoxyphenyl)-5-(2-furanyl)-1-penten-3-one, oxime 1-(3-Bromo-4-hydroxy-5-methoxyphenyl)-5-(2-furanyl)-1-pentene-3-one as prepared in Example 2 of Table 1 (9.2 g, 0.026 mole) is dissolved in methanol (500 ml) and stirred with hydroxylamine HCl (6.05 g, 0.087 mole) and sodium acetate (7.14 g, 0.087 mole) for 48 hours at room temperature. The mixture is then evaporated to dryness, redissolved in methylene chloride, and washed with water. The organic layer is then dried over sodium sulfate and concentrated to give quantitative yield of oxime (9.5 g), as an oil. Purification by flash chromatography (silica gel, chloroform:methanol 95:5 as eluent) then rechromatography using chloroform:ethyl acetate 95:5 as eluent gives 1.0 g of pure compound, mp 133°–135° C. Recrystallization from ether-hexane gives 0.7 g (7%) of (E,E)-1-(3-bromo-4-hydroxy-5-methoxyphenyl)-5-(2-furanyl)-1-penten-3-one, oxime, mp 133°–135° C. C, H, N, Br analysis: Calculated for $C_{16}H_{16}BrNO_4$, 52,48, 4.40, 3.38, 21.82); Found (52.55, 4.20), 3.53, 21.78).

EXAMPLE 28H (Z,E)-1-(3-Bromo-4-hydroxy-5-methoxyphenyl)-5-(2-furanyl)-1-pentene-3-one-oxime Further elution of the column from Example 28G with chloroform:methanol 9:1, gives an oil, which after recrystallization from ether-hexane gives 3.2 g (34%) of (Z,E)-1-(3-bromo-4-hydroxy-5-methoxyphenyl)-5-(2-furanyl)-1-penten-3-one, oxime, mp 58°–110° C. (a mixture consisting of 75% Z,E and 25% E,E isomer by NMR. C, H, N, Br analysis: Calculated for $C_{16}H_{16}BrNO_4$ (52.48, 4.40, 3.38); Found (52.45; 4.28; 3.52).

EXAMPLE 29

α-((4-Hydroxy-3,5-dimethoxyphenyl)methylidine)-β-oxo-5-(2-furan)pentanoic acid, ethyl ester, Method 1

A mixture of ethyl 5-(2-furanyl)-3-oxopentanoate[1] (157.48 g, 0.75 mol), syringic aldehyde (91.0 g, 0.5 mol), 4-methyl piperidine (4.0 g, 0.04 mol), and benzoic acid (0.97 g, 0.0078 mol) in toluene (600 ml) is heated to reflux under nitrogen for 24 hours with a water separator. The mixture is cooled, diluted with ether (1.0L) and washed successively with 5% HCl, water, $NaHCO_3$ solution, water, 5% acetic acid and then dried ($Na_2SO_4$). The solvent is removed under reduced pressure and the crude oil (212 g) is chromatographed over silica gel. Elution with methylene chloride gives the crude product as solid which is recrystallized from ether. Yield 70.7 g (37.8%), mp 103°–104° C.

[1]Matsui, et al, *J Am Chem Soc,* 1952, 74, 2182.

EXAMPLE 29A

α-[4-Hydroxy-3,5-dimethoxyphenyl)methylene]-β-oxo-5-2-furan)pentanoic acid, ethyl ester, Method 2

A mixture of ethyl-3-oxo-5(2-furyl)-pentanoate[1] (31.5 mole), syringic aldehyde (182. g, 0.1 mole) piperidine (12 ml), acetic acid (12 ml) in toluene (500 ml) is refluxed under nitrogen for 24 hours. Water is collected with a Dean-Stark trap. The mixture is cooled and washed successively with 5% hydrochloric acid, water, sodium bicarbonate solution, and water. The extract is dried over sodium sulfate and the solvent is removed under reduced pressure. The crude oil is chromatographed on silica gel column. Elution with chloroform:methanol 95:5, gives after recrystallization from isopropyl ether 2.8 g (7.5%) of α-[(4-hydroxy-3,5-dimethoxyphenyl)methylene]-β-oxo-5-(2-furan)pentanoic acid, ethyl ester, mp 103°–104° C. C, H analysis: Calculated for $C_{20}H_{22}O_7$ (64.16, 5.92); Found (64.44, 5.85).

[1]Masanao Matsui, et al, *J Am Chem Soc,* 1952, 74, 2182.

TABLE 4

[Structure: substituted phenol with OH, T, R₂ substituents connected via CH=C(CO₂C₂H₅)-C(=O)-CH₂-CH₂-[Q heterocycle]]

| Example No. | Q | T | R₂ | MP °C. | Yield % (g) | Condensing Agent | Purification Solvent | Empirical Formula | Analysis C Calcd/Found | H | N | Cl | Br | S |
|---|---|---|---|---|---|---|---|---|---|---|---|---|---|---|
| 29A1 | O | + | + | 80–82 | 9.4 (8) | Piperidine, benzoic acid | Hexane | $C_{26}H_{18}Br_2O_5$ | 73.21, 73.19, | 8.04 8.04 | | | | |
| 29A2 | O | Br | Br | 74–82 | 48 (13.6) | 4-methylpiperidine, acetic acid, benzoic acid | Isopropyl ether-hexane | $C_{18}H_{16}Br_2OS$ | 45.79, 45.77, | 3.42, 3.28, | | | 33.85 34.15 | |
| 29A3 | O | OCH₃ | Br | 97–99 | 21.2 (8.95) | 4-Methylpiperidine, benzoic acid | Methylene chloride-hexane | $C_{19}H_{19}BrO_6$ | 53.91, 53.67, | 4.52, 4.37, | | | 18.88 18.58 | |
| 29A4 | O | OCH₃ | H | 123–125 | 19 (2.6) | 4-Methylpiperidine, benzoic acid | Ethyl acetate | $C_{19}H_{20}O_6$ | 66.27, 66.27, | 5.85 5.72 | | | | |
| 29A5 | O | Cl | Cl | 72–79 | 23.7 (2.2) | 4-Methylpiperidine, acetic acid, benzoic acid | Methylene chloride-hexane | $C_{18}H_{16}Cl_2O_5$ | 66.43, 56.56, | 4.21, 4.22, | | 18.50 18.71 | | |
| 29A6 | O | + | H | 107–109 | 9.5 (1.4) | 4-Methylpiperidine, benzoic acid | Diethyl ether-isopropyl ether | $C_{22}H_{26}O_5$ | 71.33, 71.42, | 7.08 7.03 | | | | |
| 29A7 | S | CH₃ | CH₃ | 120–122 | 28.5 (10.2) | 4-Methylpiperidine, piperidine, benzoic acid | Methylene chloride-toluene | $C_{20}H_{22}O_4S$ | 67.01, 67.02, | 6.1 6.0 | | | | |
| 29A8 | O | CH₃ | CH₃ | 99–101 | 38.6 (13.2) | 4-Methylpiperidine, piperidine, benzoic acid | Toluene | $C_{20}H_{22}O_5$ | 70.16, 70.40, | 6.48 6.34 | | | | |
| 29A9 | O | CH₃ | + | 88–90 | 24 (2.4) | 4-Methylpiperidine, piperidine benzoic acid, acetic acid | Diethyl ether-hexane | $C_{23}H_{28}O_5$ | 71.85, 71.89, | 7.34 7.25 | | | | |
| 29A10 | S | + | + | 90–92 | 4.3 (1.9) | 4-Methylpiperidine, benzoic acid | Toluene-hexane | $C_{26}H_{34}O_4S$ | 70.56, 70.93, | 7.74, 7.90, | | | | 7.24 7.20 |
| 29A11 | O | + | Br | 88–91 | 31.5 (2.2) | 4-Methylpiperidine, piperidine, benzoic acid | Diethyl ether-hexane | $C_{22}H_{25}BrO_5$ | 58.81, 58.78, | 5.61, 5.60, | | | 17.78 17.48 | |
| 29A12 | S | OCH₃ | OCH₃ | 93–94 | 6.2 (2.4) | 4-Methylpiperidine, | Ethanol-water | $C_{20}H_{22}O_6S$ | 61.52, | 5.68, | | | | 8.21 |

TABLE 4-continued

[Structure: furan/thiophene (Q) connected via CH2CH2 to C(=O)C(CO2C2H5)=CH-phenyl with OH and R2 substituents, T on phenyl]

| Example No. | Q | T | R2 | MP °C. | Yield % (g) | Condensing Agent | Purification Solvent | Empirical Formula | Analysis C H N Cl Br S Calcd/Found |
|---|---|---|---|---|---|---|---|---|---|
| 29A13 | S | | Br | 91–93 | 41.2(1.98) | piperidine, benzoic acid 4-Methylpiperidine, piperidine, benzoic acid | Diethyl ether-hexane | C22H25BrO4S | 56.78, 5.41, 17.17, 6.89 / 56.76, 5.41, 17.12, 6.66 |
| 29A14 | O | OCH3 | | 112–113 | 20 (0.77) | 4-Methylpiperidine, piperidine, benzoic acid | Ethyl acetate-hexane | C23H28O6 | 68.98, 7.05 / 68.99, 7.04 |

(First row also shows: 61.50, 5.58, 8.03)

EXAMPLE 29B

α-[[3-(1,1-dimethylethyl)-4-hydroxy-5-methylphenyl]-methyene]-β-oxo-2-thiophenepentanoic acid, ethyl ester A mixture of ethyl-3-oxo-5-(2-thienyl)-pentanoate[2] (4.0 g, 0.176 mole), 3-tert-butyl-5-methyl-4-hydroxybenzaldehyde[3] (2.0 g, 0.01 mole), piperidine (0.2 g), 4-methylpiperidine (0.2 g), benzoic acid (0.2 g) in toluene (300 ml) is refluxed under nitrogen for 23 hours. Water is collected with a Dean-Stark trap. The mixture is cooled, diluted with ether (100 ml) and washed successively with 5% hydrochloric acid (2×500 ml), water (500 ml), sodium bicarbonate solution 92×500 ml), and water (2×500 ml). The extract is dried over sodium sulfate and the solvent is removed under reduced pressure. The crude oil (7 g) is chromatographed on silica gel column. Elution with methylene chloride gives after recrystallization from ethyl acetate-hexane 1.93 g (46.4%) of α-[[3-(1,1-dimethylethyl)-4-hydroxy-5-methylphenyl)-methylene]-oxo-2-thiophenepentanoic acid, ethyl ester, mp 97°–99° C. C, H, S analysis: Calculated for $C_{28}H_{28}O_4S$ (68.97, 7.05, 8.0); Found (68.72, 7.06, 8.30).

[2]Beecham Group Ltd., EP Appl. 35853 (1981).
[3]S. L. Shapiro, et al, J Org Chem, 1961, 26, 3580.

EXAMPLES 30 AND 31

The procedure described in Example 29 is repeated to prepare the following α-((4-hydroxy-3,5-disubstituted phenyl)methylidine-β-oxo-pentanoic acid, ethyl esters, starting from appropriately substituted 4-hydroxy-benzaldehyde and ethyl 5-(aryl)-3-oxo-pentanoate in presence of piperidine or methyl piperidine as base in each case:

EXAMPLE 30

α-[(4-Hydroxy-3,5-di-tert-butylphenyl)methylidine]-β-oxo-5-(2-furan)pentanoic acid, ethyl ester.

Mp 80°–2° C.

EXAMPLE 31

α-[(4-Hydroxy-3,5-dimethoxyphenyl)methylidine]-β-oxo-5-phenylpentanoic acid, ethyl ester Mp 109.5°–111.5° C. starting from ethyl 5-phenyl-3-oxo-pentanoate[4] and syringic aldehyde.

[4]E. C. Taylor et al, Org. Prep. Proceed., Int'l., 1978, 10:221.

EXAMPLE 32

α-[(4-Hydroxy-3,5-dimethoxyphenyl)methylidine]-β-oxo-5-(2-furan)pentanoic acid

A mixture of ethyl α-[(4-hydroxy-3,5-dimethoxyphenyl)methylene]-β-oxo-5-(2-furan)pentanoate (20 g, 0.053 mol) and aqueous methanolic potassium hydroxide solution [prepared from potassium hydroxide (10.6 g), water (75 ml) and methanol (125 ml)] is heated to reflux on a steam bath for 3.0 hours. Methanol is removed under reduced pressure and the residue is diluted with water (450 ml), extracted with ether and then acidified with 4N HCl. The acidic material is extracted with ethyl acetate as usual to give 6.35 g (34%) of the acid, mp 135° C. (dec). It is recrystallized from ethyl acetate to give an analytical sample, mp 135° C. (dec).

EXAMPLE 32A

1-[2-[(3,5-bis(1,1-dimethylethyl)-4-hydroxyphenyl)-methylene]-5-(2-furanyl)-1,3-dioxopentyl)-piperidine According to the procedure of Example 29, Method 2, 1-[2-[(3,5-bis-(1,1-dimethylethyl)-4-hydroxyphenyl)-methylene]-5-(2-furanyl)-1,3-dioxopentyl]-piperidine is prepared from ethyl-3-oxo-5-(2-furyl)-pentanoate (21.0 g, 0.1 mole), 3,5-di-tertbutyl-4-hydroxybenzaldehyde (12.07 g, 0.05 mole), piperidine (4 ml), acetic acid (12 ml), and toluene (500 ml).

Recrystallization from methanol gives 6.53 g (25%) of 1-[2-(3,5-bis(1,1-dimethylethyl)-4-hydroxyphenyl)-methylene]-5-(2-furanyl)-1,3-dioxopentyl]-piperidine, mp 155°–157° C. C, H, N analysis: Calculated for $C_{29}H_{39}NO_4$ (74.80, 8.44, 3.07); Found (74.85 8.41, 2.89).

EXAMPLE 33

(E)1-[(3,5-Dimethoxy-4-hydroxy)phenyl]-5-(2-furanyl)-1-penten-3-one 4-(2-Furanyl)-2-butanone (7.B g, 0.056 mol) is added to a solution of pyrrolidine (7.1 g, 0.1 mol) in acetic acid (6.0 g, 0.1 mol) and the mixture is stirred at 23° C. for 28 min. A solution of syringic aldehyde (9.8 g, 0.054 mol) in THF (70 ml) is then added dropwise and the mixture is stirred for 72 hours. The reaction mixture is added to 5% HCl and the contents are stirred for 3.0 hours. The product is extracted with ethyl acetate, dried and concentrated to give 4.95 g of residue. This is chromatographed over silica gel and eluted with $CHCl_3$—$CH_3OH$ (95:5) mixture to give a solid which is recrystallized from isopropyl ether. Yield 1.4 g (9%), mp 107°–9° C.

EXAMPLE 34

(E)4-[3,5-Bis(1,1-dimethylethyl)-4-hydroxyphenyl]-1-phenoxy-3-buten-2-one

A solution of 3,5-di-t-butyl-4-hydroxy benzaldehyde (3.75 g, 0.016 mol) and 1-phenoxy-3-(triphenylphosphoranylidene)-2-propanone (Wittig reagent)[5] (9.85 g, 0.024 mol) in xylene (200 ml) is heated under reflux for six hours in a nitrogen atmosphere. An additional amount (6.6 g; 0.016 mol) of Wittig reagent is added and refluxing continued for six more hours. The dark brown reaction mixture is filtered through silica gel 60 (60 g) and then chromatographed over silica gel eluting with 1:2-EtOAc-cyclohexane. The dark-brown fractions containing product are treated with charcoal and then rechromatographed on a flash chromatography column (75 g silica gel 60, 230–400 mesh) eluting with 10% EtOAc-cyclohexane. The isolated pure product is recrystallized from pentane as golden tan crystals (1.31 g, 22%), mp 100°–101.5° C.

[5]M. LeCorre, Bull. Soc. Chim., Fr. No. 9–10, pt. 2, 1951 (1974).

EXAMPLES 35–39

The procedure described in Example 34 is repeated to prepare the following 4-[(substituted-4-hydroxyphenyl)-1-phenoxy (or substituted phenoxy)]-3-buten-2-ones, starting from appropriately substituted-4-hydroxybenzaldehyde and appropriate Wittig reagents in each case.

| Example | T and $R_1$ | Ar | Solvent | mp |
|---|---|---|---|---|
| 35 | 3,5-$(OCH_3)_2$ | phenyl | toluene | 149–150° C. |

-continued

| Example | T and R₁ | Ar | Solvent | mp |
|---|---|---|---|---|
| 36 | 3,5-(iso-Pr)₂ | phenyl | toluene | 117–119.5° C. |
| 37 | 3,5-(t-Bu)₂ | 4-(CH₂COOCH₃)phenyl | xylene | 101.5–103° C. |
| 38 | 3,5-(OCH₃)₂ | 4-(CH₂COOCH₃)phenyl | toluene | 116.5–119.5° C. |
| 39 | 3-OCH₃ | 4-(CH₂COOCH₃)phenyl | toluene | 97–98° C. |

EXAMPLE 39A (E)-4-[[4-(4-hydroxy-3,5-dimethylphenyl)-2-oxo-3-butenyl]-oxy]-benzene acetic acid, Method C Methyl (E)-4-[[4-(4-hydroxy-3,5-dimethylphenyl)-2-oxo-3-butenyl]oxy]-benzene acetate (1.73 g) (0.00488 mole) is dissolved in 150 ml 0.1N NaOH and warmed on the steam bath. As soon as a temperature of 70° is reached the reaction mixture is removed from the bath and allowed to cool to 50°, at which point 1N HCl (17 ml) is added slowly. The precipitated solid is filtered off, washed with H₂O, and recrystallized from HOAc—H₂O to yield yellow crystals, 1.22 g (73%), mp 151°–153.5° C. Anal. for $C_{20}H_{20}O_5$: Calc. C 70.58, H 5.92; Fd. C 70.48, H 5.72.

EXAMPLE 40

(Intermediate Wittig Reagent)
1-Triphenylphosphoranylidene-3-(4'-methoxyacetyl-phenoxy)-2-propanone (A compound of the formula V wherein n is 1, Y is O and Ar is phenyl having a para substituent of the formula $CH_3O_2CCH_2$.)

A solution of methyl 4-hydroxyphenyl acetate (40 g, 0.24 mol) in dry THF (300 ml) is added to a cold (0°–5° C.) suspension of NaH (10 g, 60% oil dispersion, 0.25 mol) in THF (150 ml) over 45 min. After the addition is complete, the mixture is stirred at 23° C. for 1.5 hours. 1-Chloro-3-triphenyl phosphoranylidene)-2-propanone (77.6 g; 0.22 mol) is added in one lot to the anion and then refluxed for 5.0 hours. The reaction mixture is cooled, decomposed with acetic acid (10 ml) and then evaporated to dryness. The residue is suspended in 0.33N HCl (300 ml) and then extracted with $CH_2Cl_2$. The organic layer is washed with saturated $NaHCO_3$ solution, dried ($MgSO_4$) and evaporated to dryness. The crude product of formula V having n, Y and Ar as

TABLE 5

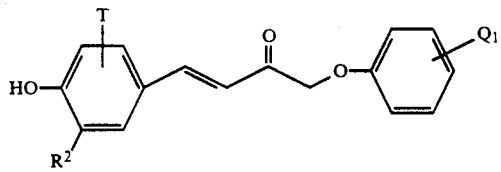

| Example | T | R² | Q₁ | M.P. | Recrystn. Solvent | Wittig Reagent Aldehyde Ratio |
|---|---|---|---|---|---|---|
| 39A1 | (CH₃)₃C— | (CH₃)₃C— | H | 100–101.5° | n Pentane | 2.5 |
| 39A2 | CH₃O | Br | H | 144–145.5° | EtOAc—C₆H₁₂ | 1 |
| 39A3 | Br | Br | H | 143–145° | EtOAc—C₆H₁₂ | 2 |
| 39A4 | CH₃O | CH₃O | 3-CH₂COOCH₃ | 99–100° | EtOAc—C₆H₁₂ | 1 |
| 39A5 | Cl | Cl | H | 140–141.5° | EtOAc | 1 |
| 39A6 | Br | Br | 4-CH₂COOCH₃ | 116–120° | EtOAc—C₆H₁₂ | 1.1 |
| 39A7 | CH₃ | CH₃ | H | 92.5–94.5° | EtOAc—n-hexane | 0.96 |
| 39A8 | CH₃ | CH₃ | 4-CH₂COOCH₃ | 133–136° | EtOAc—Et₂O | 1 |
| 39A9 | (CH₃)₃C— | (CH₃)₃C— | 3-CH₂COOCH₃ | 90.5–92.5° | n-Pentane | 1 |

| Example | Yield in Grams | % Yield | Analysis |
|---|---|---|---|
| 39A1 | 1.31 | 22 | Calc C, 78.65; H, 8.25 |
|  |  |  | Fd  C, 78.56; H, 8.44 |
| 39A2 | 3.9 | 72 | Calc C, 56.22; H, 4.16; Br, 22.00 |
|  |  |  | Fd  C, 56.48; H, 4.26; Br, 21.83 |
| 39A3 | 5.3 | 64 | Calc C, 46.63; H, 2.94; Br, 38.78 |
|  |  |  | Fd  C, 46.51; H, 2.97; Br, 38.56 |
| 39A4 | 0.8 | 10 | Calc C, 65.28; H, 5.75 |
|  |  |  | Fd  C, 65.38; H, 5.64 |
| 39A5 | 6.59 | 51 | Calc C, 59.47; H, 3.74; Cl, 21.94 |
|  |  |  | Fd  C, 59.43; H, 3.58; Cl, 21.86 |
| 39A6 | 5.3 | 55 | Calc C, 47.14; H, 3.33; Br, 33.01 |
|  |  |  | Fd  C, 47.17; H, 3.09; Br, 32.75 |
| 39A7 | 7.5 | 33 | Calc C, 76.57; H, 6.43 |
|  |  |  | Fd  C, 76.54; H, 6.53 |
| 39A8 | 2.4 | 35 | Calc C, 71.17; H, 6.26 |
|  |  |  | Fd  C, 70.97; H, 6.27 |
| 39A9 | 1.08 | 11 | Calc C, 73.95; H, 7.81 |
|  |  |  | Fd  C, 74.32; H, 7.79 | defined above is recrystallized from EtOAc as white crystals. Yield 73.5 g (63.5%), mp 143.5°-145.5° C.

EXAMPLE 40A

The procedure described in Example 40 is repeated to prepare 1-triphenylphosphoranylidene-3-3½-methoxyacetylphenoxy)-2-propanone, starting from methyl-3-hydroxyphenylacetate and appropriate Wittig reagent, mp 118°-119° C. (EtOAc-c-$C_6H_{12}$) (chromatography required). Yield 19.9 g (41%).

EXAMPLE 41

(E)-1-[(3,5-Dimethoxy-4-hydroxy)phenyl]-4-phenoxy-1-buten-3-one oxime

A solution of (E)-4-(4-hydroxy-3,5-dimethoxyphenyl)-1-phenoxy-3-buten-2-one (0.95 g, 0.003 mol) and hydroxylamine hydrochloride (0.42 g, 0.006 mol) in 1:1-pyridine-ethanol (10 ml) is heated under reflux for 2.0 hours. The reaction mixture is evaporated to near dryness and then suspended in water (50 ml) and extracted with ether. The ether extracts are evaporated to dryness and the residue is chromatographed over silica gel 60 (30 g) eluting with EtOAc-toluene (1:2). The purified product is recrystallized from $Et_2O$. Yield 0.29 g (29.4%), mp 144°-147° C.

The usefulness of the compounds of the present invention as inhibitors of lipoxygenase enzyme or other related biochemical actions is demonstrated by their effectiveness in various standard test procedures. A description of each procedure follows.

EXAMPLE 41A

4-[[4-[3,5-bid-(1,1-dimethylethyl)-4-hydroxyphenyl)-2-hydroxyimino-3-butenyl]oxy]-benzoic acid, methyl ester. Method A A solution of 4-[[4-[3,5-bis-(1,1-dimethylethyl)-4-hydroxyphenyl]-2-oxo-3-butenyl]oxy]benzoic acid, methyl ester (3.07 g, 0.007 mole), hydroxylamine HCl (1.46 g, 0.21 mole) and NaOAc (1.72 g, 0.021 mole) in 100 ml MeOH is allowed to stand at room temperature for 48 hours. The reaction mixture is evaporated to dryness and the residue is taken up in $H_2O$ and extracted with $CHCl_3$. The $CHCl_3$ extract is dried over $Na_2SO_4$ and evaporated to dryness. The residue is flash-chromatographed on silica gel, eluting with $CH_2Cl_3$ and EtOAc—$CH_2Cl_3$. The fractions containing the product are combined, yielding 1.41 g (44%) white amorphous solid, mp 53°-65° C.

Anal. for $C_{27}H_{35}NO_5$. Calculated C 71.50, H 7.78, N 3.09; Found C 71.42, H 7.81, N 2.77.

TABLE 6

| No. | T | $R_2$ | X | Y | Z | Ar | M.P. |
|---|---|---|---|---|---|---|---|
| 41A1 | $CH_3O$ | H | H | O | $CH_2O$ | 4-$C_6H_4CH_2COOH$ | 147-150° |
| 41A2 | Br | Br | H | O | $CH_2O$ | 4-$C_6H_4CH_2COOH$ | 142-166° |
| 41A3 | $CH_3$ | $CH_3$ | H | O | $CH_2O$ | 4-$C_6H_4CH_2COOH$ | 151-153.5° |
| 41A4 | Cl | Cl | H | NOH | $CH_2O$ | $C_6H_5$ | 177-181° |
| 41A5 | $(CH_3)_3C$ | $(CH_3)_3C$ | H | O | $CH_2O$ | 4-$C_6H_4CH_2COOH$ | 146-147.5° |
| 41A6 | $CH_3O$ | H | H | NOH (single isomer) | $CH_2S$ | $C_6H_5$ | 133.5-135° |
| 41A7 | $CH_3O$ | H | H | NOH | $CH_2S$ | $C_6H_5$ | 104.5-110° |
| 41A8 | $CH_3O$ | $CH_3O$ | H | O | $CH_2O$ | 3-$C_6H_4CH_2COOH$ | 126-128° |
| 41A9 | Br | Br | H | NOH | $CH_2O$ | 4-$C_6H_4CH_2COOCH_3$ | 144-153° |
| 41A10 | $CH_3$ | $CH_3$ | H | NOH (single isomer) | $CH_2O$ | $C_6H_5$ | 177-179° |
| 41A11 | Br | Br | H | NOH | $CH_2O$ | $C_6H_5$ | 179.5-180.5° |

| No. | Recrystn. Solvent | Amount Grams | % Yield | Analysis |
|---|---|---|---|---|
| 41A1 | HOAc—$H_2O$ | 0.76 | 61 | Calc C, 66.66; H, 5.30<br>Fd C, 66.38; H, 5.14 |
| 41A2 | HOAc—$H_2O$ | 0.23 | 24 | Calc C, 45.99; H, 3.00; Br, 33.99<br>Fd C, 45.76; H, 2.79; Br, 33.72 |
| 41A3 | HOAc—$H_2O$ | 1.22 | 73 | Calc C, 70.58; H, 5.92<br>Fd C, 70.48; H, 5.72 |
| 41A4 | $Et_2O$—$C_6H_{12}$ | 1.7 | 34 | Calc C, 56.82; H, 3.87; N, 4.14; Cl, 20.97<br>Fd C, 56.62; H, 3.82; N, 4.13; Cl, 21.20 |
| 41A5 | $Et_2O$—$C_6H_{12}$ | 1.37 | 81 | Calc C, 73.56; H, 7.60<br>Fd C, 73.57; H, 7.65 |
| 41A6 | $Et_2O$—$C_6H_{12}$ | 0.41 | 28 | Calc C, 64.74; H, 5.43; N, 4.44; S, 10.17<br>Fd C, 64.47; H, 5.43; N, 4.43; S, 9.87 |
| 41A7 | $CHCl_3$—$C_6H_{12}$ | 1.43 | 22 | Calc C, 64.74; H, 5.43; N, 4.44; S, 10.17<br>Fd C, 64.72; H, 5.17; N, 4.31; S, 9.95 |
| 41A8 | HOAc—$H_2O$ | 0.96 | 52 | Calc C, 64.51; H, 5.41<br>Fd C, 64.57; H, 5.46 |
| 41A9 | n-hexane | 0.56 | 37 | Calc C, 45.72; H, 3.43; N, 2.81; Br, 32.02<br>Fd C, 45.66; H, 3.40, N, 2.68; Br, 31.92 |
| 41A10 | EtOAc—n-hexane | 0.95 | 32 | Calc C, 72.71; H, 6.44; N, 4.71<br>Fd C, 72.66; H, 6.34; N, 4.53 |
| 41A11 | $Et_2O$—$C_6H_{12}$ | 0.85 | 40 | Calc C, 45.00; H, 3.07; N, 3.28; Br, 37.42<br>Fd C, 44.84; H, 3.05; N, 3.61; Br, 37.40 |

EXAMPLE 42

4-(5-Bromo-4-hydroxy-5-methoxyphenyl)-1-phenoxy-3-buten-2-one, oxime (Isomer A) and 4-(5-Bromo-4-hydroxy-5-methoxyphenyl)-1-phenoxy-3-buten-2-one, oxime (mixture of Isomer A and Isomer B)

A solution of (E)-4-(5-Bromo-4-hydroxy-5-methoxyphenyl)-1-phenoxy-3-buten-2-one (2.54 g, 0.007 mole), hydroxylamine hydrochloride (1.46 g, 0.021 mole), NaOAc 1.72 g, 0.021 mole) in 150 ml MeOH is allowed to stand for 48 hours. The reaction mixture is evaporated to dryness, taken up in $CHCl_3$ and washed with $H_2O$ and saturated NaCl. The $CHCl_3$ phase is dried over $Na_2SO_4$, evaporated to dryness, and flash-chromatographed on silica gel, eluting with $CH_2Cl_2$ and $EToAc$—$CH_2Cl_2$. The fractions yielding a single oxime isomer are collected and kept separate from those fractions containing a mixture of the oxime isomers.

The single isomer (Isomer A) fractions are washed with $Et_2O$-cyclohexane to give white crystals, 0.85 g (32%), mp 142°–145° C.

Analysis for $C_{17}H_{16}NO_4Br$: Calculated, C 53,99, H 4.26, N 3.70, Br 21.13. Found, C 53.94, H 4.11, N 3.57, Br 20.86.

The chromatography fractions containing a mixture of oxime isomers (Isomer A and Isomer B) yielded, without further purification, off-white crystals, 0.46 g (17%), mp 130°–140° C.

Analy calc for $C_{17}H_{16}NO_4Br$, C 53.99, H 4.26, N 3.70, Br 21.21; Found, C 54.10, H 4.10, N 3.52, Br, 21.07

5-Lipoxygenase Assay Using Isolated Human Leukocytes (5LOA₂)

The formation of 5-HETE in human leukocytes is considered a measure of 5-lipoxygenase activity. The protocol is described in the following.

Fresh heparinized or EDTA treated human blood is mixed with 6% dextran-3% dextrose in isotonic saline in the ratio 0.25 ml dextran solution per 1.0 ml blood. After mixing the blood is allowed to sit at room temperature for about 90 minutes while the RBC's settle. During this period, the plasma is removed with a plastic pipette to nalgens tubes.

The plasma is centrifuged at 800 rpm (125 kg) on the Beckman Td-b refrigerated centrifuge to remove the platelets (which remain in the supernatant). The pellet, consisting of leukocytes and erythrocytes, is treated with 10 ml 0.87% ammonium chloride at room temperature for four minutes, lysing the red cells. At the end of four minutes the cells are diluted with a 2× volume of phosphate buffered saline, pH 7.4, and centrifuged for ten minutes. The cells are washed three times with the phosphate buffered saline. Any of the pelleted cell matter which is not easily resuspended is discarded during the washings--the material contains platelets (12-lipoxygenase activity).

After washing, the cells are resuspended in phosphate buffered saline containing 1.0 mM calcium and 0.5 mM magnesium. After counting, the cells are diluted to $1.5-2.0\times10^{-7}$ leukocytes per milliliter.

To each poly propylene reaction tube is added 0.48 ml leukocytes in Ca-Mg phosphate buffered saline, pH 7.4; 1-5 µl test compound dissolved in DMSO and buffer; or DMSO for control tubes.

The tubes preincubate at 37° C. for five minutes.

The reaction is started by adding 20 µl of the following, 0.5 µl, 20 mM arachidonic acid--final concentration=20 µm; 1 µl, 5 mM calcium ionophore A23187—final concentration=10 µm; and 18.5 µl buffer.

The reaction proceeds for five minutes, then is stopped by adding 0.5 ml, 0.5 mM ice cold Tris buffer, pH 8.0. The tubes are chilled on ice for ten minutes and then extracted three times with a total of 3.5 ml ethyl acetate (3.0 ml removed).

The tubes can be stored at this point. For extended storage, the tubes should be filled with nitrogen.

The ethyl acetate is evaporated with a Sorvall Speed-Vac. The residue is dissolved in ethanol. The tubes can also be stored at this point at −20° C. under nitrogen.

A portion of the ethanol solution is injected into the HPLC system for 5-HETE quantitation.

The HPLC system consists of Hewlett-Packard 1040A UV spectrophotometry system with an HP85 computer. Injections are made automatically with a Waters WISP 710B. The pump is a Spectra Physics SP8700. Peaks are measured with a Hewlett Packard 3390A integrator. An RP C-18 column is used. The solvent system is isocratic; the solvent is 70% methanol and 30% 0.01M sodium acetate, pH 5.7, pumped at 1.0 ml/min. The flow is monitored at 235 nm for 5-HETE quantitation. Using a 15 cm Alltech Nucleosil C-18 5 µM column provides for a sample turnaround time of about 16 minutes.

$IC_{50}$ is calculated as the amount of test agent that causes 50% inhibition of the formation of 5-HETE relative to the control.

Cyclooxygenase Enzyme Assay (BSV)

Additionally, inhibition of cyclooxygenase is considered a measure of relevance to the pathophysiology for the above noted diseases. For example, see "Inhibition of Immunoglobulin E-Mediate, Antigen-Induced Monkey Asthma and Skin Reactions by 5,8,11,14-Eicosatetraynoic Acid," by Roy Patterson, M. D. and Kathleen E. Harris, B. S. in *J. Allergy Clin. Immunol.*, vol. 67, no. 2, pp. 146–152.

The assay consists of incubating 2 mg bovine seminal vesicle powder with 2 mM epinephrine, 2.5 mM reduced glutathione, 100 µM arachidonic acid, and the test agent for 20 minutes. The reaction mixture is acidified and extracted with ethyl acetate (3×1.0 ml) and the pooled extract is evaporated to dryness using a Speed Vac Concentrator or under a stream of nitrogen. The residue is dissolved in ethanol. An aliquot is applied on 20×20 cm silica gel plate and developed using water:ethyl acetate:hexane:acetic acid (60:54:25:12.5, upper phase) to separate $PGE_2$ from arachidonic acid. $^{14}C$-$PGE_2$ formed is identified by co-chromatography with authentic $^3H$-$PGE_2$ and the amount of radioactivity is quantitated using an automatic TLC linear scanner (Berthold, Pittsburgh, Pa.) linked to an Apple II-e computer and an $IC_{50}$ is calculated as the amount of test agent causing 50% inhibition of Cyclooxygenase Enzyme relative to the control.

The above defined value for each of tested compounds of the present invention having the noted example numbers are as found in the following Table 7.

TABLE 7

| Example No. | 5-LOA $IC_{50}$ (µM) | BSV $IC_{50}$ (µM) |
|---|---|---|
| 1 | 11.0 | |
| 2 | 1.7 | |
| 3 | 30% (20)* | |

TABLE 7-continued

| Example No. | 5-LOA<br>IC$_{50}$ (μM) | BSV<br>IC$_{50}$ (μM) |
| --- | --- | --- |
| 4 | 17% (20)* | |
| 5 | 8.8 | |
| 6 | 19% (20)* | |
| 7 | 18.0 | |
| 8 | 2.0 | |
| 9 | 15.0 | 31.0 |
| 10 | 18.0 | 92.0 |
| 11 | 22.0 | 110.0 |
| 12 | 22% (20)* | 135.0 |
| 13 | 19.0 | 84.0 |
| 14 | 11.0 | 31.0 |
| 15 | 0.079 | 169 |
| 16 | 20.0 | 130.0 |
| 16A | 12.0 | |
| 17 | 1.7 | 23.0 |
| 18 | 5.9 | |
| 19 | 1.0 | 125.0 |
| 20 | 8.7 | |
| 21 | 0.420 | 33.0 |
| 22 | 35.0 | |
| 23 (Isomer A) | 0.165 | 98.0 |
| 23 (Isomer B) | 0.26 | 90.0 |
| 24 | 2.5 | 57.0 |
| 24A | | |
| 25 | 0.71 | 170.0 |
| 26 | 3.0 | |
| 27 | | |
| 28 | | |

*% inhibition at 20 μM.

Accordingly, the present invention also includes a pharmaceutical composition for treating one of the above diseases or conditions comprising an antidisease or anticondition effective amount of a compound of the formula I as defined above together with a pharmaceutically acceptable carrier.

The present invention further includes a method for treating one of the above named diseases or conditions in mammals, including man, suffering therefrom comprising administering to such mammals either orally or parenterally, preferably oral, a corresponding pharmaceutical composition containing a compound of formula I as defined above in appropriate unit dosage form.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 1 mg to 500 mg preferably to 1 to 50 mg according to the particular application and the potency of the active ingredient. The compositions can, if desired, also contain other compatible therapeutic agents.

In therapeutic use as described above, the dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

As used herein cardiovascular diseases or conditions particularly include 1) reductions of the extent of infarct damage in a myocardial infarction, 2) prevention of recurrent myocardial infarction, 3) stroke, 4) anaphylactic shock, and 5) vasospastic disease.

An additional advantageous benefit of the cytoprotective property of the compounds of formula I are for use, for example, to protect against damage from various GI tract conditions.

Generally accepted assays can be used to measure cytoprotective activity.

The magnitude of a prophylactic or therapeutic dose of a compound of formula I will, of course, vary with the nature of the severity of the condition to be treated and with the particular compound of formula I and its route of administration. In general, the daily dose range for antiasthmatic, antiallergic or antiinflammatory use and, generally uses other than cytoprotection, lies within the range of from about 10 µg to about 20 mg per kg body weight of a mammal, preferably from about 50 µg to about 20 mg per kg of body weight of a mammal, and most preferably from about 100 µg to about 10 mg per kg of body weight of a mammal.

The exact amount of a compound of the formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the formula I in avoiding future damage would be co-administration of a compound of the formula I with a nonsteroidal antiinflammatory drug (for example, indomethacin) that might otherwise cause such damage. For such use, the compound of formula I is administered from 30 minutes prior up to 30 minutes after administration of the NSAID. Preferably, it is administered prior to or simultaneously with the NSAID (e.g. as a combination dosage form).

The effective daily dosage level for compounds of formula I inducing cytoprotection in mammals, especially humans, will generally range from about 0.002 mg/kg to about 100 mg/kg, preferably from about 0.02 mg/kg to about 30 mg/kg. The dosage may be administered in single or divided individual doses.

Thus, in addition to the compounds of formula I, the pharmaceutical compositions can also contain other active ingredients, such as cyclooxygenase inhibitors, nonsteroidal antiinflammatory drugs (NSAIDs), peripheral analgesic agents such as zomepirac, diflunisal and the like. The weight ratio of the compound of the formula I to the second active ingredient may be varied and will depend upon the effective dose of each ingredient. Generally, an effective dose of each will be used. Thus, for example, when a compound of the formula I is combined with an NSAID, the weight ratio of the compound of the formula I to the NSAID will generally range from about 1000:1 to about 1:1000, preferably about 200:1 to about 1:200. Combinations of a compound of the formula I and other active ingredients will generally also be within the aforementioned range, but in each case, an effective dose of each active ingredient should be used.

Combinations of a compound of the formula I and other active ingredients will generally be in the aforementioned ratios.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Structurally related propionic acid derivatives having similar analgesic and antiinflammatory properties are also intended to be included in this group.

Thus, "propionic acid derivatives" as defined herein are nonnarcotic analgesics/nonsteroidal antiinflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and antiinflammatory properties are also intended to be encompassed by this group.

Thus, "acetic acid derivatives" as defined herein are nonnarcotic analgesics/nonsteroidal antiinflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: mefenamic acid, meclofenamic acid, flufenamic acid, niflumic acid and tolfenamic acid. Structurally related fenamic acid derivatives having similar analgesic and antiinflammatory properties are also intended to be encompassed by this group.

Thus, "fenamic acid derivatives" as defined herein are nonnarcotic analgesics/nonsteroidal antiinflammatory drugs which contain the basic structure:

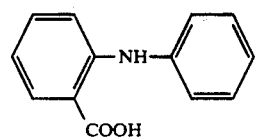

which can bear a variety of substituents and in which the free —COOH group can be in the form of a pharmaceutically acceptable salt group, e.g., —COO⁻Na⁺.

The biphenylcarboxylic acid derivatives which can be used comprise: diflunisal and flufenisal. Structurally related biphenylcarboxylic acid derivatives having similar analgesic and antiinflammatory properties are also intended to be encompassed by this group.

Thus, "biphenylcarboxylic acid derivatives" as defined herein are nonnarcotic analgesics/nonsteroidal antiinflammatory drugs which contain the basic structure:

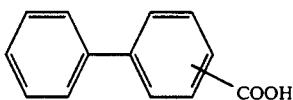

which can bear a variety of substituents and in which the free —COOH group can be in the form of a pharmaceutically acceptable salt group, e.g., —COO⁻Na⁺.

The oxicams which can be used in the present invention comprise: piroxicam, sudoxicam, isoxicam and 4-hydroxyl-1,2-benzothiazine 1,1-dioxide 4-(N-phenyl)-carboxamide. Structurally related oxicams having similar analgesic and antiinflammatory properties are also intended to be encompassed by this group.

Thus, "oxicams" as defined herein are nonnarcotic analgesics/non-steroidal antiinflammatory drugs which have the general formula:

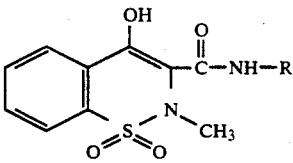

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin clonixinate, meclofenamate sodium, meseclazone, microprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

Finally, NSAIDs which may also be used include the salicylates, specifically aspirin, and the phenylbutazones, and pharmaceutically acceptable salts thereof.

Pharmaceutical compositions comprising the formula I compounds may also contain as the second active ingredient, antihistaminic agents such as benadryl, dramamine, histadyl, phenergan and the like. Alternatively, they may include prostaglandin antagonists such as those disclosed in European Patent Application 11,067 or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the formula I may also be advantageously combined with an H₁ or H₂-receptor antagonist, such as for instance cimetidine, ranitidine, terfenadine, famotidine, aminothiadiazoles disclosed in EP 81102976.8 or temelastine, acrivastine, loratadine, cetrizine, tazifylline, azelastine and like compounds, such as those disclosed in U.S. Pat. Nos. 4,283,408; 4,362,736; 4,394,508 and European Patent Application No. 40,696. The pharmaceutical compositions may also contain a K⁺/H⁺ ATPase inhibitor such as omeprazole, disclosed in U.S. Pat. No. 4,255,431, and the like. Each of the references referred to in this paragraph is hereby incorporated herein by reference.

We claim:

1. Benzeneacetic acid, 4-[[4-(4-hydroxy-3,5-dimethoxyphenyl)-2-oxo-3-butenyl]oxy]-, (E)-, benzeneacetic acid, 3-[2-oxo-3-(triphenylphosphoranylidene)-propoxy]-, methyl ester, benzeneacetic acid, 4-[[4-(4-hydroxy-3-methoxyphenyl)-2-oxo-3-butenyl]oxy]-, (E)-, benzeneacetic acid, 4-[[4-(3,5-dibromo-4-hydroxyphenyl)-2-oxo-3-butenyl]oxy]-, (E)-, benzeneacetic acid, 4-[[4-4-hydroxy-3,5-dimethylphenyl)-2-oxo-3-butenyl]oxy]-, (E)-, 3-buten-2-one, 4-(3,5-dichloro-4-hydroxyphenyl)-1-phenoxy-, oxime, benzeneacetic acid, 4-[[4-[[4-[3,5-bis(1,1-dimethylethyl)-4-hydroxyphenyl]-2-oxo-3-butenyl]oxy]-, (E)-, 3-buten-2-one, 4-(4-hydroxy-3-methoxyphenyl)-1-(phenylthio)-, oxime, 3-buten-2-one, 4-(4-hydroxy-3-methoxyphenyl)-1-(phenylthio)-, oxime (E)-, benzeneacetic acid, 3-[[4-(4-hydroxy-3,5-dimethoxyphenyl)-2-oxo-3-butenyl]oxy]-, (E)-, benzeneacetic acid, 4-[4-(3,5-dibromo-4-hydroxyphenyl)-2-(hydroxyimino)-3-butenoxy]-, 3-buten-2-one, 4-(4-hydroxy-3,5-dimethylphenyl)-1-phenoxy-, oxime, 3-buten-2-one, 4-(3,5-dibromo-4-hydroxyphenyl)-1-phenoxy-, oxime, 3-buten-2-one, 4-(3-bromo-4-hydroxy-5-methoxyphenyl)-1-phenoxy-, (E)-, 3-buten-2-one, 4-(3,5-dibromo-4-hydroxyphenyl)-1-phenoxy-, (E)-, benzeneacetic acid, 3-[[4-(4-hydroxy-3,5-dimethoxyphenyl)-2-oxo-3-butenyl]oxy]-, methyl ester, 3-buten-2-one, 4-(3,5-dichloro-4-hydroxyphenyl)-1-phenoxy-, (E)-, benzeneacetic acid, 4-[[4-(3,5-dibromo-4-hydroxyphenyl)-2-oxo-3-butenyl]oxy]-, methyl ester, 3-buten-2-one, 4-(4-hydroxy-3,5-dimethylphenyl)-1-phenoxy-, (E)-, benzeneacetic acid, 4-[[4-(4-hydroxy-3,5-dimethylphenyl)-2-oxo-3-butenyl]oxy]-, methyl ester (E)-, benzeneacetic acid, 3-[[4-(3,5-bis(1,1-dimethylethyl)-4-hydroxyphenyl)-2-oxo-3-butenyl]oxy]-, methyl ester (E)-, benzeneacetic acid, 4-[4-[3,5-bis(1,1-dimethylethyl)-4-hydroxyphenyl]-2-(hydroxyimino)-3-butenoxy]-, methyl ester, 3-buten-2-one, 4-(3-bromo-4-hydroxy-5-methoxyphenyl)-1-phenoxy-, oxime.

* * * * *